United States Patent [19]

Järvinen et al.

[11] Patent Number: 4,942,769

[45] Date of Patent: Jul. 24, 1990

[54] METHOD OF TESTING CORES

[75] Inventors: Markku S. Järvinen, Huutjärvi; Mikael J. H. Nováky; Heikki P. J. Rommi, both of Karhula, all of Finland

[73] Assignee: A. Ahlstrom Corporation, Noormarkku, Finland

[21] Appl. No.: 241,478

[22] Filed: Sep. 8, 1988

[30] Foreign Application Priority Data

Sep. 21, 1987 [FI] Finland .................................. 874103

[51] Int. Cl.⁵ ........................................... G01N 19/00
[52] U.S. Cl. ........................................ 73/82.1; 73/866
[58] Field of Search ................ 73/821, 824, 866.4, 73/866, 799, 843, 845

[56] References Cited

U.S. PATENT DOCUMENTS

| | | | |
|---|---|---|---|
| 3,593,573 | 7/1971 | Ely | 73/821 X |
| 3,858,442 | 1/1975 | Nozaki | 73/821 X |
| 3,992,928 | 11/1976 | Thoms | 73/821 X |
| 4,799,382 | 1/1989 | Sprunt et al. | 73/821 X |
| 4,807,465 | 2/1989 | Botzolakis et al. | 73/821 X |

FOREIGN PATENT DOCUMENTS

| | | | |
|---|---|---|---|
| 183406 | 8/1966 | U.S.S.R. | 73/821 |
| 896517 | 1/1982 | U.S.S.R. | 73/821 |

OTHER PUBLICATIONS

"Measurement of Contact Stress Distribution Roll Load and Roll Torque During Cold Strip Rolling", 12–14, Jan. 1982, vol. 1, pp. 98–116; by F. Al-Selihi; (source publication name missing but apparently German) in 73/824.

Primary Examiner—Tom Noland
Attorney, Agent, or Firm—Nixon & Vanderhye

[57] ABSTRACT

The loading capacity of a core manufactured by reeling and gluing from paper or board layers, is tested by dynamically loading the core under conditions that simulate real life conditions. The core is mounted on a chuck, and the method is practiced by loading the core by utilizing a roll that exerts a nip pressure, and by rotating the core. One or both of the loading and the speed of rotation of the core are changed over time in a predetermined manner, to simulate the real life conditions. For example the loading on the core can be increased constantly while the rotational speed is kept constant, or the rotational speed is increased and the loading decreased corresponding to the real use situation caused by unwinding of a paper roll which is mounted by the core. The method also includes detecting any changes in the structure of the core, either optically, by sensing vibrational changes, or by sensing the break of an electrical wire passing through the core. Loading is continued until the core breaks. One or both of the rotational speed of the core and the force loading of the core are sensed at the moment of change, and/or the time elapsed until the moment of change is detected. A sleeve may be provided on the core to contact the roll, the sleeve protecting the surface of the core and distributing the loading caused by the roll contact, to a wider area.

19 Claims, 3 Drawing Sheets

METHOD OF TESTING CORES

BACKGROUND AND SUMMARY OF THE INVENTION

The present invention relates to a method of testing the loading capacity of cores. The method according to the invention is especially suitable for testing, for example, the strength of board cores used in the paper industry.

Known cores used in the paper industry comprise several, for example 25–30, thin, e.g. 0.5–1.0 mm, and narrow, about 100 to 200 mm wide, board tapes, which are joined by glueing and spirally winding by a special machine to form a tube-like product, which is used, for example, as a core of paper and plastic rolls.

Known methods for testing cores are almost completely based on static testing. Examples of different types of methods in this group are methods based on definition of radical compression strength, axial compression strength, torsional strength, expansive strength, bending strength and like values. With these methods neither the loading situation nor the loading method corresponds the conditions which the core encounters in reality. Additionally, the break mechanism effected by said types of testing methods differs considerably from the breaks that occur in reality. Such methods are also not capable of finding all defects existing in the core, such as one insufficient glue seam or a weak board layer.

On the other hand, there are also a number of dynamic testing methods for cores, such as utilization of the vibration resulting from rotating the core on a test bench and loading of the core rotating on a chuck with a belt. Although these methods are considerably better than the above mentioned static methods due to their dynamics, even the dynamic methods do not correspond accurately to loading situations. For example, the vibration in the test bench reflects a different characteristic than the loading strength of the core when rolling.

The various methods referred to above do not provide information with sufficient reliability and accuracy about the loading strength of board cores in real rolling situations. Therefore a new type dynamic testing method for cores has been developed. The core is loaded in a manner corresponding the real conditions of center winders and unwinding means of printing presses, whereby the stress exerted on the core by the weight of the paper roll on the chuck can be simulated.

The method according to the present invention for testing the loading capacity of a core or the like member is characterized by mounting the core on a chuck and dynamically loading the core by means of a roll to simulate actual conditions of use wherein the loading of the core and/or the rotational speed are changed relative to time in a predetermined manner until the core breaks; and detecting changes in the core structure and recording the rotational speed and/or the force loading the core at the moment of change and/or the time elapsed at the moment of change.

The following advantages are obtained, for example, by the method and of the invention compared with known methods of testing cores:

a break mechanism as well as break surface end form correspond to real situations;

the method detects even a slightest defect in glueing or board in the core;

good correlation is effected in practice to the roll weights reached by different core qualities;

stress and testing time of the core to be tested correspond better to real life situations; and the testing apparatus communicates with an automatic indicator of a break point, and there is also direct reporting of the results.

DETAILED DESCRIPTION OF THE DRAWINGS

Figure 1:
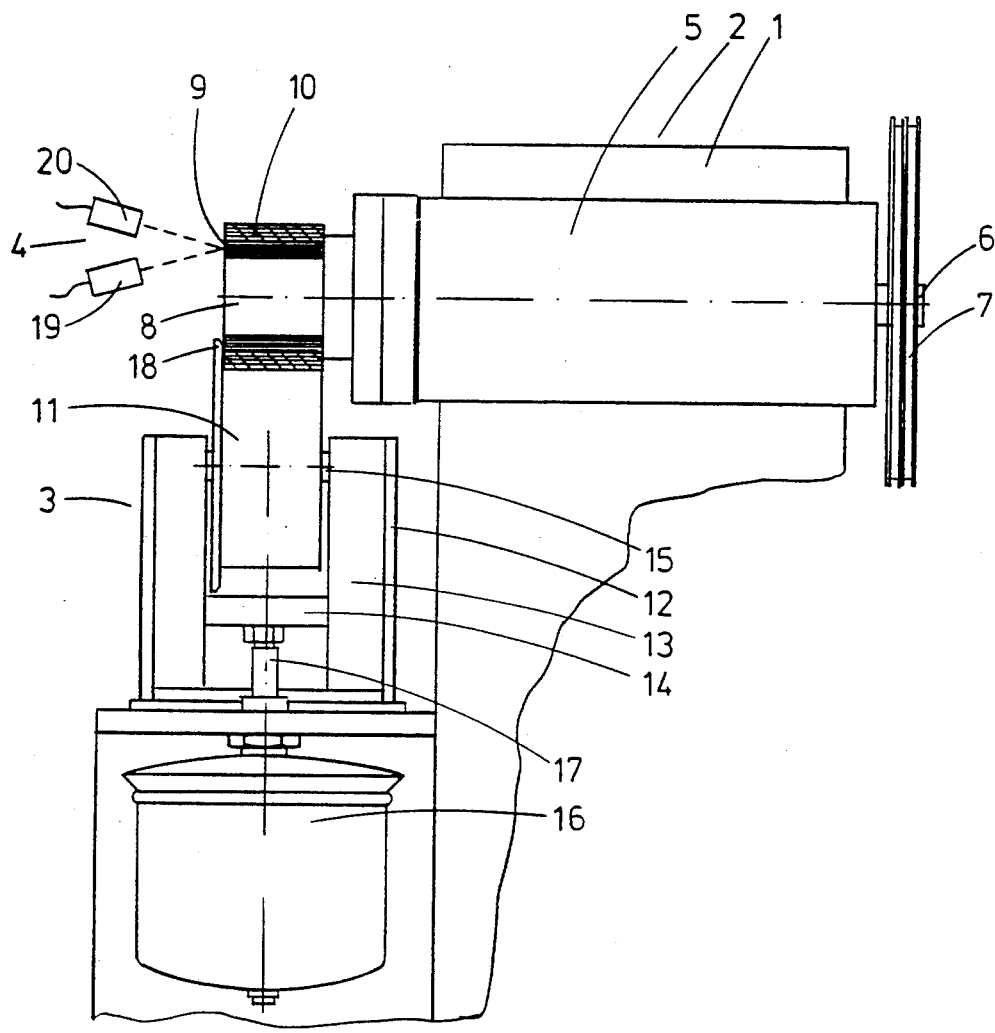
FIG. 1 is a schematic side view of part of an apparatus for testing cores, applicable in the realization of a method in accordance with the invention.

FIG. 1 illustrates an apparatus for testing cores, which is mounted on a body construction 1. The testing apparatus comprises in principle three main elements: a support apparatus 2 for the core to be tested, loading apparatus 3 and a detector device 4 for detecting and indicating the effects of the loading. The support apparatus 2 for the core includes a supporting installation 5 mounted on the body construction 1, a shaft 6 mounted with bearings in the supporting installation 5. In this embodiment a belt pulley or roller 7 is arranged on one end of the shaft, by which the shaft can be operated. On the other end of the shaft there is a chuck 8, which can be varied and thus different types of apparatus using cores can be simulated. The core 9 to be tested is located on the chuck 8 a load sleeve 10 is also mounted on core 9 to prevent the loading apparatus 3 from breaking the surface of the core 9 distributes the loading more uniformly on the surface of the core 9, exactly corresponding a real use situation. The chuck can be any type of chuck commonly used in apparatus using cores, whereby it is also possible to study the force exerted by the chuck on the inner surface of the core.

The loading apparatus 3 includes a roller 11 for pressing the core 9 via the load sleeve 10, which roller 11 is mounted with bearings on a shaft 15 mounted on a carriage 14 slidable in the guide bars 13 of the body 12 of the loading apparatus 3. The carriage 14 is vertically displaceable on the guide bars 13 and is connected by a bar 17 in the embodiment shown in the figure to the pneumatic cylinder 16 mounted on body 12 of loading apparatus 3. A flange 18 is provided on roll 11 to prevent core 9 and sleeve 10 from sliding off from chuck 8 in a loading situation.

The exemplary detector device 4 indicates the stress caused by the loading and comprises a light source 19, by means of which the edge of the core rotating on chuck 8 is illuminated, and a light detector 20, which measures the intensity of light reflecting from the edge of the core. When during the loading of core 9 via load sleeve 10 by roll 11, for example, delamination of the board or opening of the glueing between two board layers due to a glue fault occurs in the core a narrow rim-like gap is formed in the edge of the core, which gap does not reflect light to the detector, whereby the measuring device registers the temporary pressure of roll 11 against load sleeve 10. Although a load sleeve is used on the core in the above example, which can be, for example nylon, it is, of course, possible to load cores without a sleeve, whereby the coating of the loading roll can be slightly resilient, if required, so as not to make load stressing the core exactly linear.

Figure 2A:
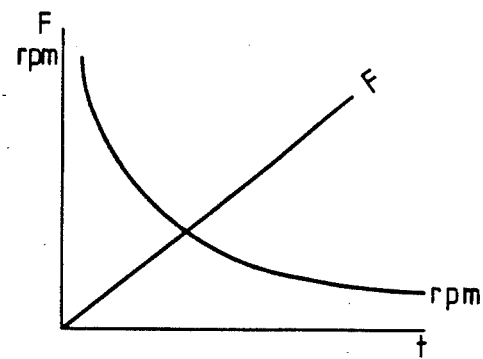
FIGS. 2a, b and c are graphs illustraing the testing principles applicable in the method according to the invention.
Figure 2B:
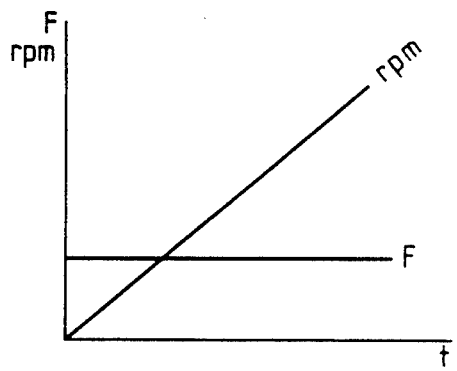
Figure 2C:
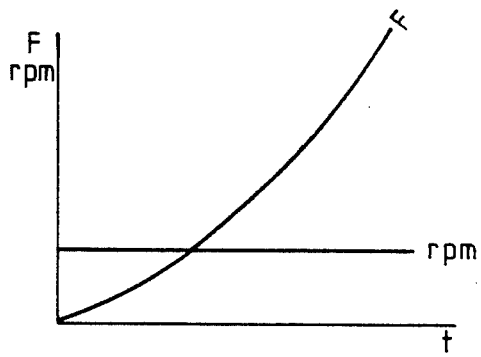
Figure 3:
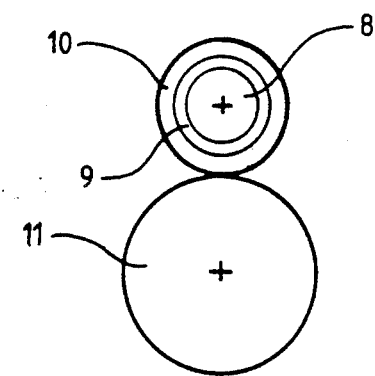
FIG. 3 is a schematic partial view of the central parts of an apparatus for practicing the method of the present invention.

The vertical axis used in the coordinates of FIGS. 2a–c represents the loading (F) and the rotational speed (rpm) and the horizontal axis represents the time (t).

FIG. 2a represents a testing method, in which the loading is evenly increased and the rotational speed decreased. In other words a situation is illustrated, in which a paper web is reeled to a roll on a core, the loading against the core is at its minimum at the beginning and, respectively, the rotational speed at its maximum varying, when the roll is reeled, according to the figure. In principle, a corresponding figure is formed when the roll is unwound, thereby FIG. 2a is to be read from the right to the left.

FIG. 2b represents a testing method, in which the rotational speed is evenly increased and the loading is maintained constant during the whole time.

FIG. 2c represents a testing method, in which the rotational speed is maintained constant and the loading is increased. Such kinds of experiments also differ slightly from the usual loading conditions but are useful for testing some special cores. In addition to the above described measuring methods it is possible to study, for example, the effects of a pulsating loading, because in practice there can sometimes be vibrations in the reeling, which cause a pulsating loading. According to the invention it is possible to provide a wholly automatic testing action, typically by utilizing a microcomputer or microprocessor to control or direct the testing. The utilization of a microcomputer or microprocessor with the heretofore described apparatus is straight-forward and well within the skill of those in the art.

The apparatus for practicing the method according to the invention also includes a data collecting or storage unit, which registers the stress directed to the core via roll 11 and the rotational speed on the ground of the information coming from registration device 4 for the stresses. Such units are typically well known microprocessors, it is not considered necessary to give a detailed description of their construction and operation. By connecting the measurements, for example, to be registered by a micro computer, it is possible to carry out necessary calculations or other definitions at the same time. It is possible to define a force or weight which breaks the core for every type of a core to be tested by determining by calculation the corresponding weight from the value of the loading strength.

It is also possible to determine a core suitable for a particular purpose on the basis of a core of particular size and strength. In other words, when the strength directed against the core in the object of use is knowm, it is possible on the basis of practical knowledge to calculate the core type presumably suitable for the particular purpose.

By carrying out the testing according to the invention, it can be determined whether the type of core tested is exactly suitable, or whether it is possible to choose a less expensive and/or somewhat weaker core, or whether a next larger size should possibly be chosen. Thus the method according to the invention enables the selection of the most suitable core for the user for each purpose without a risk of breaking the core.

As is to be noted from the above description there is developed a new type of testing method for cores, which is simple, but at the same time reliable and which can accurately simulate real life situations. However, while only one embodiment described in detail is introduced above, the inventive concept includes many different modifications within the scope of invention defined by the accompanying claims. Thus it is possible to alternatively arrange a loading roll to be used, whereby it alone would revolve the sleeve, the core and the chuck with the shaft. Furthermore, it is possible that both said members might be used at the uniform speed, whereby the frictional effects or factors can be eliminated or minimized. As for the observation equipment, it can also differ from the above described which should only be considered an example of a device generally operating optically. Other possible alternatives are various vibration bulbs, which indicate the moment when a radical change in the core takes place, such as a tear in some of the cardboard layers, or the loosening of the glueing between the layers. Additionally, it is possible to arrange a thin wire leading an electric current across the layers, whereby the rupture of the bonding between the layers and the sliding of the layers relative to each other causes the breaking of the wire and thus an easily registrable alarm. Of course, it is possible and in some cores sufficient to effect visual observation such as with a stroboscope, whereby the equipment is not totally automatic, as it can be in the other described embodiments. This kind of observation is also not very reliable and quick, but it can be sufficient in some embodiments of the applications of the method in accordance with the invention. Finally, it should be noted that although the method according to the invention is described in testing cores, it can be applied just as well in testing other products of same form and subject to similar stress.

We claim:

1. A method of testing, by dynamic loading simulating real life conditions, the loading capacity of a core manufactured by reeling and gluing from paper or board layers, the core mounted on a chuck, and utilizing a roll, said method comprising the steps of:
   (a) loading the core mounted on a chuck by exerting a nip pressure on the core with the roll;
   (b) rotating the core in contact with the roll;
   (c) changing one or both of the loading and rotational speed over time in a predetermined manner; and
   (d) detecting any changes in the structure of the core.

2. A method as recited in claim 1 comprising the further step (e) of detecting one or both of the rotational speed of the core and the force loading on the core at the moment of a change in the core.

3. A method as recited in claim 2 wherein step (c) is practiced by constantly increasing the load on the core until the core breaks.

4. A method as recited in claim 1 comprising the further step of detecting or registering one or both of the rotational speed of the core and the force loading on the core of the time elapsed until the moment of a change in the core.

5. A method as recited in claim 4 wherein step (c) is practiced by constantly increasing the load on the core until the core breaks.

6. A method as recited in claim 1 comprising the further step (e) of detecting one or both of the rotational speed of the core and the force loading on the core at the moment of change in the core, and the time elapsed until the moment of change in the core.

7. A method as recited in claim 6 wherein step (c) is practiced by constantly increasing the load on the core until the core breaks.

8. A method as recited in claim 1 utilizing a light source and an end face of the core, and wherein step (d) is practiced by optically detecting light reflected from the light source off the end face of the core.

9. A method as recited in claim 8 utilizing a sleeve mounted on the core for protecting the surface of the core and distributing the loading caused by the roll to a wider area, and wherein step (a) is practiced by the loading the core by contacting the sleeve with the roll.

10. A method as recited in claim 1 wherein step (d) is practiced by sensing the vibration caused by a change in the structure of the core.

11. A method as recited in claim 1 wherein the core is layered, and utilizing an element leading an electric current across the layers of the core; and wherein step (d) is practiced by sensing a break in the electric current carrying member.

12. A method as recited in claim 1 wherein step (c) is practiced by constantly increasing the load on the core until the core breaks.

13. A method as recited in claim 12 wherein step (c) is practiced by increasing the load on the core at a rate that corresponds to the real growth speed of the weight the core will be subjected to during actual use.

14. A method as recited in claim 12 wherein step (c) is practiced so that the loading on the core is increased at a rate that is higher than the real growth speed of the weight loading that a core will be subjected to in actual use.

15. A method as recited in claim 12 wherein step (b) is practiced by keeping the rotational speed of the core essentially constant.

16. A method as recited in claim 12 utilizing a sleeve mounted on the core for protecting the surface of the core and distributing the loading caused by the roll to a wider area, and wherein step (a) is practiced by the loading the core by contacting the sleeve with the roll.

17. A method as recited in claim 1 wherein step (c) is practiced to change the rotational speed of the core as a function of time corresponding to the slowdown of the rotational speed of the core during actual use of the core.

18. A method as recited in claim 1 wherein step (c) is practiced by increasing the rotational speed of the core and decreasing the loading on the core to corresponding to a real use situation caused by the unwinding of a paper roll associated with the core.

19. A method as recited in claim 1 utilizing a sleeve mounted on the core for protecting the surface of the core and distributing the loading caused by the roll to a wider area, and wherein step (a) is practiced by the loading the core by contacting the sleeve with the roll.

* * * * *